(12) United States Patent
Ebel et al.

(10) Patent No.: US 8,404,220 B2
(45) Date of Patent: Mar. 26, 2013

(54) PRODUCTION OF ADAPALENE GELS

(75) Inventors: Maurice Ebel, Poisy (FR); Richard Dugat, Rumilly (FR)

(73) Assignee: Galderma Research & Development, Biot (FR)

( * ) Notice: Subject to any disclaimer, the term of this patent is extended or adjusted under 35 U.S.C. 154(b) by 307 days.

(21) Appl. No.: 12/786,885

(22) Filed: May 25, 2010

(65) Prior Publication Data

US 2010/0280121 A1 Nov. 4, 2010

Related U.S. Application Data

(63) Continuation of application No. PCT/EP2008/066339, filed on Nov. 27, 2008.

(60) Provisional application No. 60/996,618, filed on Nov. 27, 2007.

(30) Foreign Application Priority Data

Nov. 27, 2007 (EP) .................................. 07121665

(51) Int. Cl.
*A61K 8/72* (2006.01)
*A61K 31/19* (2006.01)
*A61P 17/10* (2006.01)

(52) U.S. Cl. ..................................... 424/70.11; 514/569
(58) Field of Classification Search ............... 424/70.11; 514/569

See application file for complete search history.

(56) References Cited

U.S. PATENT DOCUMENTS

| | | | |
|---|---|---|---|
| 2003/0170196 A1 | 9/2003 | Orsoni et al. | |
| 2005/0059740 A1 | 3/2005 | Graeber et al. | |
| 2007/0148110 A1 | 6/2007 | Zanutto et al. | |
| 2008/0175810 A1 * | 7/2008 | Zhang | 424/78.05 |

FOREIGN PATENT DOCUMENTS

| WO | WO 2006/048747 A1 | 5/2006 |
|---|---|---|
| WO | WO 2007/031883 A2 | 3/2007 |

OTHER PUBLICATIONS

International Search Report corresponding to PCT/EP 2008/066339 mailed Feb. 9, 2009.

* cited by examiner

*Primary Examiner* — Aradhana Sasan
(74) *Attorney, Agent, or Firm* — SNR Denton US LLP

(57) ABSTRACT

A method for producing an adapalene aqueous gel on an industrial scale including formulating a gelling medium A by mixing water and propylene glycol and adding a gelling agent thereto; formulating an adapalene medium B by dispersing adapalene in water, in the presence of a surfactant; next adding the adapalene medium B to the gelling medium A; and adjusting the pH to about 4.7-5.3.

19 Claims, 1 Drawing Sheet

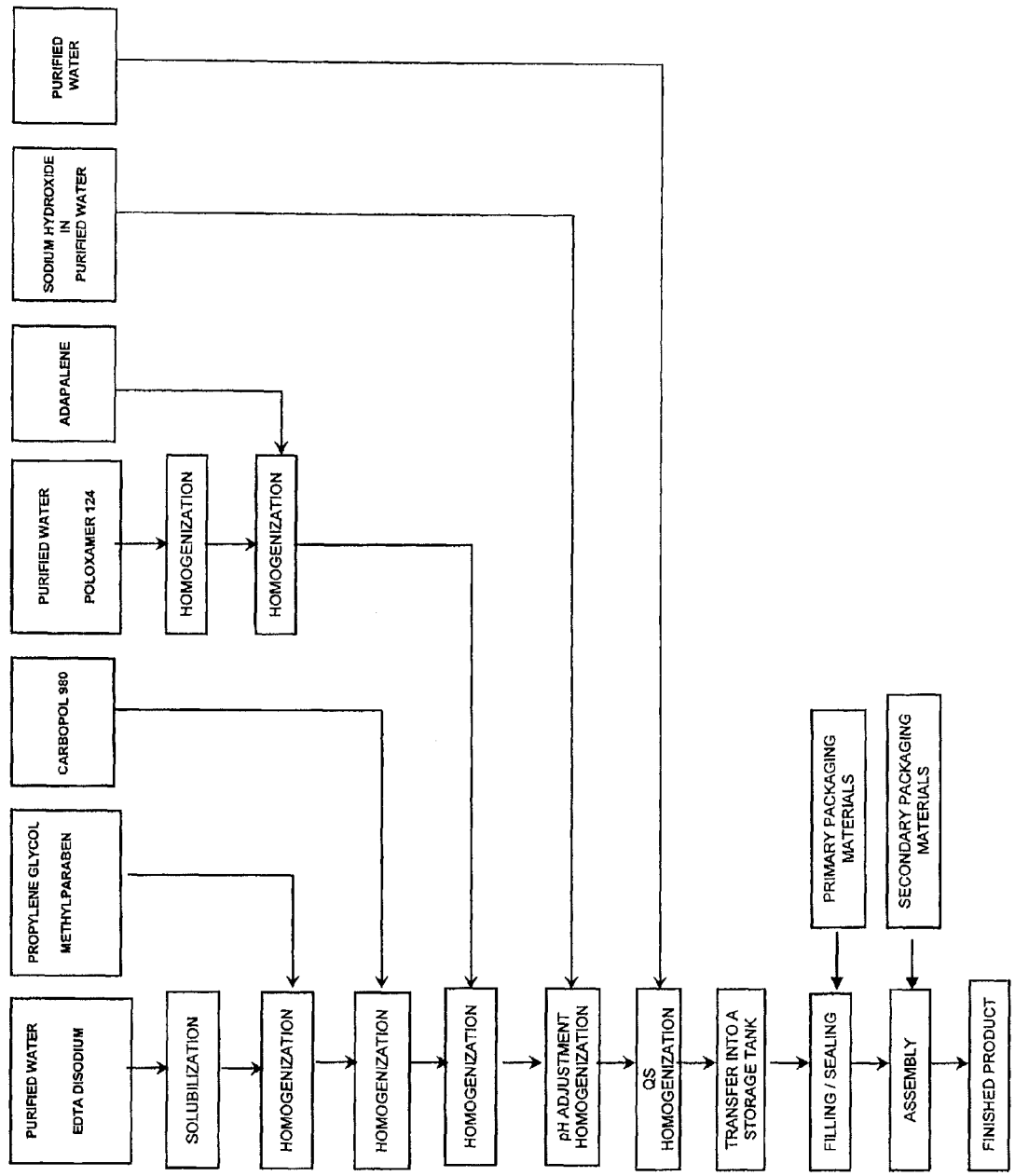

PRODUCTION OF ADAPALENE GELS

CROSS-REFERENCE TO EARLIER APPLICATIONS

This application is a continuation of PCT/EP 2008/066339, filed Nov. 27, 2008 and designating the United States (published in the English language on Jun. 4, 2009 as WO 2009/068610 A1), which claims foreign priority under 35 U.S.C. §119 of EP 07121665.9, filed Nov. 27, 2007, and also claims benefit under 35 U.S.C. §119(e) of U.S. Provisional Application No. 60/996,618, filed Nov. 27, 2007, each hereby expressly incorporated by reference in its entirety and each assigned to the assignee hereof.

BACKGROUND OF THE INVENTION

1. Technical Field of the Invention

The present invention relates to the domain of manufacturing processes and features the production of adapalene aqueous gels on an industrial level.

2. Description of Background and/or Related and/or Prior Art

Adapalene is a retinoid derived from naphthoic acid. It is 6-[3-(1-adamantyl)-4-methoxyphenyl]-2-naphthoic acid and is described in EP-0199636. A method for synthesizing this compound is described in EP-0358574.

Adapalene is marketed in the form of an alcoholic solution, an aqueous gel and a cream, at a weight concentration of 0.1%. These compositions are useful for the treatment of acne.

WO 03/075908 describes the administration of adapalene at a weight concentration of 0.3% in an aqueous gel, for the treatment of dermatological disorders.

Classical formulation processes are known that require a mixture to be cooled to obtain an adequate mixing of all ingredients and which necessitate additional industrial equipment.

Thus, need remains for an improved process for the production of aqueous gels of adapalene at the industry level.

SUMMARY OF THE INVENTION

A novel and advantageous method for producing adapalene aqueous gels on an industrial level has now been developed.

The present invention thus features a method for producing an adapalene aqueous gel, which method comprises the steps of:
i) preparing a gelling medium A by mixing water and propylene glycol and adding a gelling agent thereto;
ii) preparing an adapalene medium B by dispersing adapalene in water, in the presence of a surfactant;
with the proviso that said steps i) and ii) are carried out in parallel or any of step i) or ii) is carried out after the other;
iii) adding the adapalene medium B to the gelling medium A;
iv) adjusting the pH thereof,
whereby a gel is formed.

In one specific embodiment, the gelling agent in step i) is added after propylene glycol.

In another specific embodiment the pH is adjusted to about 4.7-5.3

For the purpose of the above method, each step is advantageously carried out at room temperature. Therefore, drawbacks of classical formulation processes are overcome with the present invention.

In addition, the medium A may further contain a preservative agent which is dissolved in propylene glycol at room temperature. The preservative agent is preferably methylparaben.

Furthermore, the medium A may further contain a chelating agent and preferably EDTA disodium which is dissolved in water before addition of propylene glycol and the gelling agent. The gelling agent is preferably Carbopol 980.

In a preferred embodiment of the invention, the surfactant is a non-ionic surfactant and preferentially a block copolymer surfactant and more preferred a poloxamer, for example poloxamer 182, poloxamer 124 and is preferentially Poloxamer 124 (Polyethylene-Polypropylene Glycol also known as Pluronic® L44).

The adapalene quantity ranges from 0.01% to 1%, preferably from 0.1% to 0.3% and the weight ratio of adapalene/water in the adapalene medium B is from 6% to 23% to preferably from 6% to 20%;

In one specific embodiment of the invention, the said method comprises the steps of:
i) preparing a gelling medium A by mixing and dissolving/solubilizing EDTA disodium in water, adding propylene glycol and methylparaben, mixing and adding Carbopol® 980, wherein the proportion of propylene glycol/water ranges from 4% to 5% and preferably is about 4.5%; separately
ii) dispersing adapalene in water in the presence of Poloxamer 124, whereby an adapalene medium B is obtained wherein the proportion of adapalene/active phase and the weight ratio of adapalene/water in the adapalene medium B ranges from 6% to 23% to preferably from 6% to 20%;
iii) adding the adapalene medium B to the gelling medium A;
iv) adding sodium hydroxide to adjust the pH.

In the said method, the sodium hydroxide is added after step (iii).

In a specific embodiment, the pH is adjusted to about 4.7-5.3.

The present invention also features an adapalene gel obtained by the said method and the gel produced following the method as described earlier.

According to the present description, "an adapalene aqueous gel" means a gelified aqueous composition, that is preferably monophasic, and that contains adapalene, preferably as a sole active ingredient that exhibits a cosmetic or therapeutic effect, and preferably in a dispersed state.

Adapalene is present in the gel in a therapeutically efficient amount. It ranges from 0.001% to 5% and preferably ranges from 0.01% to 1% in weight, typically from 0.1% to 0.3% in weight, with regard to the total weight of the aqueous gel. In a preferred embodiment 0.3% is preferred.

The addition of propylene glycol at a very early stage in the process is a particular feature of the invention. By very early stage it should be understood the first step and particularly in step i) of the process. Therefore, in a specific embodiment, the gelling agent in step i) is added after propylene glycol.

The present invention features a specific embodiment of the solubilization of the preservative in the propylene glycol at 1 to 10%, preferably about 4-5%. This preservative agent is advantageously present in a quantity sufficient for inhibiting microbial growth in the gel during storage and particularly at 0.01% to 3% with regard to the total weight of the aqueous gel.

The preservative agent is advantageously selected from among the following agents: benzalkonium chloride, bronopol, chlorhexidin, chlorocresol and derived products thereof, ethylic alcohol, phenethylic alcohol, phenoxyethanol, potassium sorbate, benzylic alcohol, diazolidinylurea, parabens, or mixture thereof.

This preservative agent is preferably selected from the paraben family. For example, it can be methylparaben.

This solubilization is obtained advantageously at room temperature, with common stirring equipment at low or moderate speed. This represents an advantage for a manufacturing process as it avoids heating the gelling medium A, so at industrial level, this invention advantageously reduces manufacturing duration and energy required.

In a particular embodiment, medium A may further comprise a chelating agent. The chelating agent is advantageously selected from among the following: ethylene diamine tetraacetic acid (EDTA), diethylene triamine pentaacetic acid (DTPA), ethylene diamine-di (O-hydroxyphenyl acetic acid (EDDHA), hydroxy-2-ethylene diamine triacetic acid (HEDTA), ethyldiamine-di (O-hydroxy-p-methyl phenyl) acetic acid (EDDHMA) and ethylene diamine-di (5-carboxy-2-hydroxyphenyl) acetic acid (EDDCHA).

In a preferred embodiment, the chelating agent is ethylene diamine tetraacetic acid (EDTA) or one of its salts, such as EDTA disodium, as an additional ingredient. EDTA or its salts is useful to chelate metal cations that may be present as impurities in the composition, which makes it possible to avoid side effects in certain patients. EDTA further inhibits browning of the composition during storage of the gel. The gels prepared according to the method of the invention advantageously contain EDTA, or its salts, preferably EDTA disodium, in an amount of 0.05 to 0.5%, typically about 0.1%.

In a preferred embodiment, EDTA, or EDTA disodium, is dissolved in water before addition of propylene glycol and the gelling agent.

The gelling agent is adapted to make a gel out of an aqueous medium. It is preferably a hydrodispersible polymer that exhibits a high affinity with water. This polymer preferably contains free carboxylic groups that are all or partly neutralized in a form of carboxylate through the use of a base. Preferred gelling agents are vinyl polymers with hydrodispersible carboxylate groups, such as a polyacrylic acid gel, that is neutralized by a base, e.g., sodium hydroxide. Also preferred are polymers with a molecular weight of about 1,250,000 to 4,000,000. Crosslinked polyacrylic acids such as polyacrylic acid reticulated with polyalkenyl polyethers are also encompassed. For example, suitable gelling agent are selecting from the following list: electrolyte-insensitive carbomers, marketed with the trademark Ultrez 20®, Carbopol 1382 or Carbopol ETD2020® by BF Goodrich, polysaccharides such as xanthan gum, e.g., Xantural180® marketed by Kelco, guar gum, chitosans, carrageenans, cellulose and the derivatives therefrom such as hydroxypropylmethylcellulose particularly, the product marketed under the trademark Methocel E4 premium by Dow Chemical or hydroxyethylcellulose, particularly the product marketed under the trademark Natrosol HHX 250® by Aqualon, family of aluminum magnesium silicates such as Veegum K marketed by Vanderbilt, family of acrylic polymers coupled with hydrophobic chains such PEG-150/decyl alcohol/SMDI copolymer marketed under the trademark Aculyn 44 (polycondensate comprising at least as element one polyethyleneglycol with 150 or 180 moles of ethylene oxide, decyl alcohol and methylene bis(4-cyclohexylisocyanate) (SMDI), 35% by weight in a mixture of propylene glycol (39%) and water (26%)), family of modified starch such as potato starch marketed under the trademark Structure Solanace or mixture thereof, family of polyacrylamides such as the mixture Sodium acryloyldimethyltaurate copolymer/isohexadecane/polysorbate 80 marketed under the trademark Simulgel 600 by Seppic, mixture polyacrylamide/isoparaffin C13-14/laureth-7 such the product marketed under the trademark Sepigel 305 by Seppic.

Suitable preferred gelling agents include the family of polymers and preferably those called carbomer polymers which are a crosslinked polyacrylate polymer such as carbomer 940, i.e., Carbopol® 980 (2-Propenoic acid, polymer with 2,2-bis(hydroxymethyl)propane-1,3-diol 2-propenyl ether) by the Goodrich or family of polyacrylamides and preferably those called Simulgel 600 or Sepigel 305.

The gels prepared according to the invention preferably contain from about 0.5% to about 2% of the gelling agent, preferably about 1%, e.g., 1.1%. The weight ratio of the gelling agent/water in medium A may range 1% to 1.5%.

Adapalene medium B, that is advantageously prepared in parallel, is typically a medium wherein adapalene is dispersed.

Advantageously, the weight ratio of adapalene/water in the adapalene medium B ranges from 6% to 23% to preferably from 6% to 20%. Medium B preferably comprises a surfactant. The surfactant may preferably be selected from ethylene oxide and propylene oxide block copolymers, and their mixtures, and, preferably, the gel is devoid of any surfactant other than ethylene oxide and propylene oxide block copolymers.

The ethylene oxide and propylene oxide block copolymers which can be used as surfactant in the nanoemulsion of the invention can be selected, in particular, from the block copolymers of formula (I) $HO(C_2H_4O)_x(C_3H_6O)_y(C_2H_4O)_zH$, wherein x, y, and z are integers such that x+z ranges from 2 to 100 and y ranges from 14 to 60, and their mixtures, and more particularly the above block copolymers having an HLB (Hydrophilic Lipophilic Balance) ranging from 2 to 16.

These block copolymers can be selected, in particular, from poloxamers and in particular from Poloxamer 231, such as the product marketed by ICI under the name Pluronic® L81, of formula (I) where $x=z=6$ and $y=39$ (HLB 2); Poloxamer 282, such as the product marketed by ICI under the name Pluronic® L92, of formula (I) where $x=z=10$ and $y=47$ (HLB 6); and most preferably Poloxamer 124, such as the product marketed by ICI under the name Pluronic® L44, of formula (I) where $x=z=11$ and $y=21$ (HLB 16).

In a preferred embodiment, the suitable surfactants have an HBL from 7 to 9, or many non-ionic of polyoxyethylene and/or polyoxypropylene copolymers type. They must be liquid so as to be incorporated easily in the composition without it being necessary to heat it.

The surfactants can be classified, according to their structure, under the generic terms "ionic" (anion, cation, amphoteric) or "non-ionic". The non-ionic surfactants are those which do not dissociate in ions in water and are thus insensitive with the variations of pH.

Among the surfactants, preferred are those of the family of Poloxamers and more particularly Poloxamer 124 and/or Poloxamer 182 or such as the propylene glycol, the dipropylene glycol, the propylene glycol dipelargonate, the lauroglycol, the ethoxydiglycol, the sodium docussate.

The gels prepared according to the invention may comprise such surfactant in an amount of about 0.1% to about 0.5%, preferably about 0.2%.

The amount of surfactant in medium B can range, for example, from 0.01% to 0.4% by weigh with respect to the total weight of medium B.

The neutralization of the carboxylic groups in the gelling polymers may be achieved by adding a neutralizing agent selected from a base, such as ammonia, sodium hydroxide, organic amines such as alkylamine, or dialkylamine, trialkyamine, alkanolamine, or dialkanolamine. Said alkylamine can be selected from methylamine, ethylamine. The pH of the final mixture, i.e., after mixing the adapalene medium B in the gelling medium A, is adjusted to about 4.7-5.3.

In a preferred embodiment, the invention provides a method which comprises the steps of:
i) preparing a gelling medium A by mixing and optionally dissolving/solubilizing the chelating agent such as EDTA disodium in water, adding propylene glycol and optionally the preservative agent such as methylparaben, mixing, and adding the gelling agent such as Carbopol® 980 (or Carbomer 940), wherein the proportion of propylene glycol/water ranges from 4% to 5% and preferably is about 4.5%; separately
ii) dispersing adapalene in water in the presence of a surfactant such as Poloxamer 124, whereby an adapalene medium B is obtained wherein the proportion of adapalene/active phase ratio to water ranges from 6% to 20%;
iii) adding the adapalene medium B to the gelling medium A;
iv) adjusting the pH to about 4.7-5.3 by adding a neutralizing agents such as sodium hydroxide Another feature of the present invention is an adapalene gel produced via the method of manufacture described above. Particularly, the present invention features a gel produced following this method. Preferably, the gel comprises 0.3% of adapalene.

This gel is of particular interest for the treatment of dermatological ailments with an inflammatory or proliferative component, selected from:
common acne (acne vulgaris), comedones, polymorphous acne, nodulocystic acne, acne conglobata, secondary acne such as solar, drug-related or occupational acne,
widespread and/or severe forms of psoriasis, ichtyoses and ichtyosiform states;
Darier's disease;
actinic keratoses;
palmo plantar keratoderma and keratosis pilaris;
leucoplasias and leucoplasiform states, lichen planus;
any benign or malignant, severe and extensive dermatological preparations.

The gel is particularly suitable for the treatment of acne, such as common acne, and in particular for the treatment of common acne of moderate to moderately severe intensity.

In order to further illustrate the present invention and the advantages thereof, the following specific examples are given, it being understood that same are intended only as illustrative and in nowise limitative. In said examples to follow, all parts and percentages are given by weight, unless otherwise indicated.

BRIEF DESCRIPTION OF THE DRAWING

FIG. 1 is a flow diagram that illustrates the manufacturing process for the adapalene gel.

EXAMPLES

Example 1

Manufacturing Process of Adapalene Gel 0.3% (2000 kg)

The manufacturing process for commercial production of Adapalene Gel, 0.3% is described as follows. See FIG. 1 also.
Carbomer Medium:
a) In a suitably sized, stainless steel primary compounding vessel, purified water is added (88.92%)
b) It is placed under a dissolver and mixed.
c) The pre-weighed quantity of Edetate Disodium (0.10%) is added and mixed.
d) In a stainless steel container, using a dissolver, the pre-weighed quantities of propylene glycol (4%) and methylparaben (0.2%) are added and mixed until completely dissolved.
e) The propylene glycol/methylparaben solution is added to the primary compounding vessel and mixed.
f) While mixing, the pre-weighed quantity of Carbomer 940 (Carbopol 980) is added (1.10%).
g) The mixing is maintained until the medium is smooth.
Adapalene Medium:
a) In another stainless steel vessel, the specified quantity of purified water (1%) is added and mixed.
b) The pre-weighed quantities of Poloxamer 124 (0.2%) and Adapalene (0.3%) are added.
c) Mixing is maintained until the adapalene is dispersed.
d) The adapalene medium is mixed with a dissolver.
Primary Compounding Phase:
a) The adapalene medium is transferred to the carbomer medium.
b) The medium newly obtained is mixed.
Final Compounding Phase:
a) The batch is moved to a counter-motion mixer and mixed.
b) A solution of pre-weighed sodium hydroxide (0.18%) is prepared with purified water (1%) in a separate container and added to the primary compounding phase.
c) The batch is mixed.
d) pH is checked and recorded (Range: 4.7-5.3).
e) If pH is within range, the remaining volume of purified water is added qsp 100%. If pH is below or above the specified range, the batch is adjusted with a solution of hydrochloric acid or sodium hydroxide to pH 5.0±0.3.
Product Testing, Filling, and Packaging:
a) Using a transfer pump, the product is filtered through an 80 mesh filter screen to the filler.
b) The bulk product is filled into the specified tubes. The lot code and expiration date are applied to the tube-end seal during the tube sealing operation.
c) Representative samples of the packaged product are submitted for testing.
d) Secondary packaging is performed, so that the finished product is obtained.

Example 2

Manufacturing Process of Adapalene Gel 0.1% (2000 kg)

The manufacturing process for commercial production of Adapalene Gel, 0.1% is described as follows. See FIG. 1 also.
Carbomer Medium:
a) In a suitably sized, stainless steel primary compounding vessel, purified water is added (88.92%)
b) It is placed under a dissolver and mixed.
c) The pre-weighed quantity of Edetate Disodium (0.10%) is added and mixed.
d) In a stainless steel container, using a dissolver, the pre-weighed quantities of propylene glycol (4%); phenoxyethanol and methylparaben (0.1%) are added and mixed until completely dissolved.
e) The propylene glycol/methylparaben solution is added to the primary compounding vessel and mixed.
f) While mixing, the pre-weighed quantity of Carbomer 940 (Carbopol 980) is added (1.10%).
g) The mixing is maintained until the medium is smooth.

Adapalene Medium:
a) In another stainless steel vessel, the specified quantity of purified water (1%) is added and mixed.
b) The pre-weighed quantities of Poloxamer 182 (0.2%) and Adapalene (0.1%) are added.
c) Mixing is maintained until the adapalene is dispersed.
d) The adapalene medium is mixed with a dissolver.

Primary Compounding Phase:
a) The adapalene medium is transferred to the carbomer medium.
b) The medium newly obtained is mixed.

Final Compounding Phase:
a) The batch is moved to a counter-motion mixer and mixed.
b) A solution of pre-weighed sodium hydroxide (0.18%) is prepared with purified water (1%) in a separate container and added to the primary compounding phase.
c) The batch is mixed.
d) pH is checked and recorded (Range: 4.7-5.3).
e) If pH is within range, the remaining volume of purified water is added qsp 100%. If pH is below or above the specified range, the batch is adjusted with a solution of hydrochloric acid or sodium hydroxide to pH 5.0±0.3.

Product Testing, Filling, and Packaging:
a) Using a transfer pump, the product is filtered through an 80 mesh filter screen to the filler.
b) The bulk product is filled into the specified tubes. The lot code and expiration date are applied to the tube-end seal during the tube sealing operation.
c) Representative samples of the packaged product are submitted for testing.
d) Secondary packaging is performed, so that the finished product is obtained.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for producing an adapalene aqueous gel, which method comprises the steps of:
   i) formulating a gelling medium A by mixing water, propylene glycol and a preservative agent, and adding a gelling agent thereto;
   ii) formulating an adapalene medium B by dispersing adapalene in water, in the presence of a surfactant;
   with the proviso that steps i) and ii) are carried out in parallel or any of step i) or ii) is carried out after the other;
   iii) adding the adapalene medium B to the gelling medium A; and
   iv) adjusting the pH by adding neutralizing agent thereto, whereby a gel is formed, said adapalene being in a dispersed state in said gel; said adapalene being the sole active ingredient that exhibits a cosmetic or therapeutic effect in said gel; and all steps in said method being conducted at room temperature.

2. The method as defined by claim 1, wherein the gelling agent is added in step i) after propylene glycol.

3. The method as defined by claim 1, wherein the pH is adjusted to about 4.7 to 5.3.

4. The method as defined by claim 1, wherein the preservative agent is dissolved in propylene glycol at room temperature.

5. The method as defined by claim 1, wherein the preservative agent comprises methylparaben.

6. The method as defined by claim 1, wherein said medium A also contains a chelating agent.

7. The method as defined by claim 6, wherein EDTA (ethylene diamine tetraacetic acid) disodium chelating agent is dissolved in water before addition of propylene glycol and the gelling agent.

8. The method as defined by claim 1, wherein the gelling agent comprises 2-propenoic acid, polymer with 2,2-bis(hydroxymethyl)propane-1,3-diol 2-propenyl ether.

9. The method as defined by claim 1, wherein the surfactant comprises a poloxamer.

10. The method as defined by claim 9, wherein the poloxamer comprises Poloxamer 124.

11. The method as defined by claim 1, wherein the gel comprises adapalene in an amount ranging from 0.01% to 1% by weight.

12. The method as defined by claim 1, wherein the weight ratio of adapalene/water in the adapalene medium B ranges from 6% to 23%.

13. The method as defined by claim 1, which comprises the steps of:
   i) formulating a gelling medium A by mixing and dissolving EDTA disodium in water, adding propylene glycol and methylparaben, mixing and adding 2-propenoic acid, polymer with 2,2-bis(hydroxymethyl)propane-1, 3-diol 2-propenyl ether, wherein the proportion of propylene glycol/water ranges from 4% to 5%;
   ii) separately dispersing adapalene in water in the presence of Poloxamer 124, whereby an adapalene slurry medium B is obtained wherein the proportion of adapalene/active phase and the weight ratio of adapalene/water in the adapalene slurry medium B ranges from 6% to 23%;
   iii) adding the adapalene slurry medium B to the gelling medium A; and
   iv) adding sodium hydroxide to adjust the pH to about 4.7 to 5.3; whereby a gel is formed, said adapalene being in a dispersed state in said gel; said adapalene being the sole active ingredient that exhibits a cosmetic or therapeutic effect in said gel; and all steps in said method being conducted at room temperature.

14. The method as defined by claim 1, wherein sodium hydroxide is added after step (iii).

15. The method as defined by claim 6, wherein the chelating agent comprises EDTA sodium.

16. The method as defined by claim 1, wherein the gel comprises adapalene in an amount of 0.1% to 0.3% by weight.

17. The method as defined by claim 1, wherein the gel comprises adapalene in the amount of 0.3% by weight.

18. The method as defined by claim 13, wherein the gel comprises adapalene in an amount of 0.1% to 0.3% by weight.

19. The method as defined by claim 13, wherein the gel comprises adapalene in the amount of 0.3% by weight.

* * * * *